(12) United States Patent
Soldin et al.

(10) Patent No.: US 9,012,835 B2
(45) Date of Patent: Apr. 21, 2015

(54) METHODS FOR SIMULTANEOUS QUANTIFICATION OF THYROID HORMONES AND METABOLITES THEREOF BY MASS SPECTROMETRY

(75) Inventors: Steven J. Soldin, Bethesda, MD (US); Offie P. Soldin, Bethesda, MD (US)

(73) Assignee: Georgetown University, Washington, DC (US)

( * ) Notice: Subject to any disclaimer, the term of this patent is extended or adjusted under 35 U.S.C. 154(b) by 190 days.

(21) Appl. No.: 13/881,602

(22) PCT Filed: Nov. 7, 2011

(86) PCT No.: PCT/US2011/059583
§ 371 (c)(1),
(2), (4) Date: May 17, 2013

(87) PCT Pub. No.: WO2012/087438
PCT Pub. Date: Jun. 28, 2012

(65) Prior Publication Data
US 2014/0361156 A1     Dec. 11, 2014

Related U.S. Application Data

(60) Provisional application No. 61/411,257, filed on Nov. 8, 2010.

(51) Int. Cl.
*G01N 33/487* (2006.01)
*G01N 33/68* (2006.01)
(Continued)

(52) U.S. Cl.
CPC .......... *G01N 33/487* (2013.01); *G01N 33/6848* (2013.01); *G01N 33/78* (2013.01); *G01N 30/7233* (2013.01); *G01N 33/492* (2013.01); *H01J 49/26* (2013.01)

(58) Field of Classification Search
USPC ............................................. 250/252.1, 282
See application file for complete search history.

(56) References Cited

U.S. PATENT DOCUMENTS

| 2011/0282587 A1* | 11/2011 | Jones et al. ..................... 702/19 |
| 2012/0244627 A1 | 9/2012 | Soldin |
| 2012/0309105 A1 | 12/2012 | Soldin |

FOREIGN PATENT DOCUMENTS

WO    WO-2012/012719 A2    1/2012

OTHER PUBLICATIONS

Piehl, S. et al., "Development of a validated liquid chromatography/tandem mass spectrometry method for the distinction of thyronine and thyronamine constitutional isomers and for the identification of new deiodinase substrates", *Rapid Communications in Mass Spectrometry*, 22(20):3286-3296 (John Wiley & Sons, Ltd., Oct. 30, 2008).

(Continued)

*Primary Examiner* — Kiet T Nguyen
(74) *Attorney, Agent, or Firm* — Alan W. Steele; Foley Hoag LLP

(57) ABSTRACT

The invention provides methods for simultaneously detecting or simultaneously quantifying any combination of thyroxine ($T_4$), triiodothyronine ($T_3$), 3,3'-diiodo-L-thyronine ($3,3'$-$T_2$), 3-iodothyronamine ($T_1$AM), and, optionally, reverse $T_3$ ($rT_3$) in a sample obtained from a human. The method involves a simple, sensitive, accurate, and specific isotope dilution tandem mass spectrometry method for the simultaneous quantification of any combination of $T_4$, $T_3$, $3,3'$-$T_2$, $T_1$AM, and, optionally, $rT_3$ in a sample obtained from a human, e.g., in human plasma or serum samples. This assay is far more sensitive than previously described assays for thyronamines and allows quantitation of $T_1$AM in human plasma or serum, including from healthy controls.

18 Claims, 2 Drawing Sheets

(51) Int. Cl.
  *G01N 33/78* (2006.01)
  *G01N 30/72* (2006.01)
  *G01N 33/49* (2006.01)
  *H01J 49/26* (2006.01)

(56) References Cited

OTHER PUBLICATIONS

Soldin, O. P. et al., "Thyronamines: Tandem Mass Spectrometry Quantification in Biological Fluids", *Thyroid Hormone Metabolism and Regulation*, 19(1):S114-S115 (USA, Sep. 26, 2009).

Soldin, O. P. et al., "Thyronamines in Humans: Development of a Validated Isotope Dilution Liquid Chromatography/Tandem Mass Spectrometry Method for Their Management.", *Endocrine Reviews; 92nd Meeting and Expo of the Endocrine Society*, 31(3)(Supp. 1):S2303 (The Endocrine Society, San Diego, CA, USA, Jun. 1, 2010).

International Search Report and Written Opinion of the International Searching Authority from parent patent application PCT/US2011/059583 dated Feb. 24, 2012.

* cited by examiner

METHODS FOR SIMULTANEOUS QUANTIFICATION OF THYROID HORMONES AND METABOLITES THEREOF BY MASS SPECTROMETRY

GOVERNMENT SUPPORT

This invention was made with government support under NIH GCRC grant M01-RR-020359 and NICHD grant 5U10HD047890-03NIH. The government has certain rights in this invention.

RELATED APPLICATIONS

This application is the U.S. national phase of International Patent Application No. PCT/US2011/059583, filed Nov. 7, 2011, which claims benefit of priority under 35 U.S.C. 119(e) to U.S. Provisional Patent Application No. 61/411,257, filed on Nov. 8, 2010.

BACKGROUND

Iodothyronines and thyronamines are two classes of endogenous signaling molecules which contain different numbers and/or the positions of iodine atoms [1]. The iodothyronines thyroxine ($T_4$), triiodothyronine ($T_3$), and diiodothyronines ($T_2$s) are important in regulating a number of biological processes, which include regulating long bone growth and fetal neuronal development, increasing the basal metabolic rate and the body's sensitivity to catecholamines, and affecting protein synthesis and oxygen consumption [3,4]. Thyronamines are decarboxylated metabolites of the iodothyronines [2].

The thyronamine 3-iodothyronamine ($T_1AM$) is a decarboxylated and deiodinated derivative of thyroxine ($T_4$) with biological effects contrary to that of $T_3$ [5]. $T_1AM$ has been shown to activate the trace amine-associated receptor (TAAR1), a G protein-coupled receptor (GPCR) activated by monoamines and amphetamine-related psychostimulants [6-8]. Details of the physiology and pharmacology of $T_1AM$ have yet to be elucidated, particularly in normal subjects. Using currently available methods, the amount of $T_1AM$ in normals is below detectable limits. In vivo, administration of $T_1AM$ in large doses has been demonstrated to induce decreased metabolic rate, hypothermia, bradycardia, hypotension, hyperglycemia, and increased lipid versus carbohydrate metabolism [5, 9-13].

Serum $T_4$ and $T_3$ concentrations are most commonly measured by immunoassays. However, these immunoassays lack specificity and are susceptible to various interferences, particularly during pregnancy, when maternal thyroid hormones are crucial to fetal brain development [14-16]. At this time an immunoassay to measure $T_1AM$ has yet to be developed.

Mass spectrometry methods, especially isotope dilution liquid chromatography tandem mass spectrometry (LC-MS/MS) methods, have been developed in recent years to measure $T_3$ and $T_4$ in human serum or plasma [17-19]. Scanlan and colleagues described LC-MS/MS methods to detect $T_1AM$ from rodent brain, heart and liver tissues [5,10] and also from rodent and human serum [20]. Although $T_1AM$ has been observed in vivo and the concentrations detected from rodent or human serum are estimated below 5 nM (1.8 μg/L) [5,12, 20], clinically relevant quantification of endogenous $T_1AM$ remains a challenge.

SUMMARY OF THE INVENTION

The present invention provides a highly sensitive, rapid, and clinically relevant method to measure, simultaneously, any combination of $T_1AM$, $T_4$, $T_3$, 3,3'-diiodo-L-thyronine (3,3'-$T_2$), and, optionally, reverse $T_3$ ($rT_3$) in a sample obtained from a human. In one embodiment the present invention provides a highly sensitive, rapid, and clinically relevant method to measure, simultaneously, $T_1AM$, $T_4$, $T_3$, and 3,3'-$T_2$ in a sample obtained from a human. In one embodiment the present invention provides a highly sensitive, rapid, and clinically relevant method to measure, simultaneously, $T_1AM$, $T_4$, $T_3$, 3,3'-$T_2$, and $rT_3$ in a sample obtained from a human. The present invention also provides a method to quantify $T_1AM$, including endogenous $T_1AM$, in human plasma or serum at concentrations <100 pg/mL (281 pmol/L). The method involves a simple, sensitive, accurate, and specific isotope dilution tandem mass spectrometry method for the simultaneous quantification of any combination of $T_1AM$, $T_4$, $T_3$, 3,3'-$T_2$, and, optionally, $rT_3$ in a sample obtained from a human, e.g., in human plasma or serum samples. This assay is far more sensitive than previously described assays for thyronamines [1] and allows quantitation of $T_1AM$ in human plasma or serum from healthy controls.

The invention may be of particular use in the clinical assessment and treatment of any of a variety of diseases and conditions including hypertension, congestive heart failure, diabetes mellitus, pregnancy, and attention deficit disorder, in addition to thyroid disease per se.

An aspect of the invention is a method of simultaneously assaying thyroxine ($T_4$), triiodothyronine ($T_3$), 3,3'-diiodo-L-thyronine (3,3'-$T_2$), and 3-iodothyronamine ($T_1AM$). The method includes the steps of:

a) providing a test sample, wherein the test sample comprises $T_4$, $T_3$, 3,3'-$T_2$, and $T_1AM$;

b) providing a calibration sample, wherein the calibration sample comprises known quantities of reference $T_4$, $T_3$, 3,3'-$T_2$, and $T_1AM$;

c) combining the test sample with the calibration sample;

d) determining by mass spectrometry the quantity of $T_4$, $T_3$, 3,3'-$T_2$, and $T_1AM$ in the test sample and the quantity of the reference $T_4$, $T_3$,3,3'-$T_2$, and $T_1AM$; and e) calibrating the quantity of the $T_4$, $T_3$, 3,3'-$T_2$, and $T_1AM$ in the test sample against the known and determined quantities of the reference $T_4$, $T_3$, 3,3'-$T_2$, and $T_1AM$ in the calibration sample.

In one embodiment, each of the reference $T_4$, $T_3$, 3,3'-$T_2$, and $T_1AM$ is differentially labeled with one or more mass spectrometrically distinct groups, such that each of the test sample $T_4$, $T_3$, 3,3'-$T_2$, and $T_1AM$ and each of the reference $T_4$, $T_3$, 3,3'-$T_2$, and $T_1AM$ can be distinguished by mass spectrometry.

In one embodiment, each of the reference $T_4$, $T_3$, 3,3'-$T_2$, and $T_1AM$ is radioisotopically labeled.

In one embodiment, the reference $T_4$ is deuterium-labeled $T_4$.

In one embodiment, the reference $T_3$ is $^{13}$C-labeled $T_3$.

In one embodiment, the reference 3,3'-$T_2$ is $^{13}$C-labeled 3,3'-$T_2$.

In one embodiment, the reference $T_1AM$ is deuterium-labeled $T_1AM$.

In one embodiment, the method further includes separating components of the combined sample of step (c) by liquid chromatography prior to step (d).

In one embodiment, the test sample is obtained from a human.

In one embodiment, the test sample is selected from the group consisting of blood, serum, plasma, amniotic fluid, and cerebrospinal fluid.

In one embodiment, the test sample further comprises reverse $T_3$ ($rT_3$); the calibration sample further comprises a known quantity of reference $rT_3$; the determining further comprises determining by mass spectrometry the quantity of $rT_3$ in the test sample and the quantity of the reference $rT_3$; and the calibrating further comprises calibrating the quantity of the $rT_3$ in the test sample against the known and determined quantity of the reference $rT_3$ in the calibration sample.

In one embodiment, the reference $rT_3$ is deuterium-labeled $rT_3$.

In one embodiment, the reference $rT_3$ is $^{13}$C-labeled $rT_3$.

In one embodiment, the determining the test sample $T_1AM$ comprises detecting as little as 2.5 pg/mL (7.0 pmol/L). In one embodiment, the detection limit for $T_1AM$ in the test sample is 2.5 pg/mL (7.0 pmol/L).

In one embodiment, the determining the test sample $T_1AM$ comprises quantitating as little as 4.0 pg/mL (11.3 pmol/L). In one embodiment, the quantitation limit for $T_1AM$ in the test sample is 4.0 pg/mL (11.3 pmol/L).

In one embodiment, the determining the test sample $3,3'-T_2$ comprises detecting as little as 2.5 pg/mL (4.8 pmol/L). In one embodiment, the detection limit for $3,3'-T_2$ in the test sample is 2.5 pg/mL (4.8 pmol/L).

In one embodiment, the determining the test sample $3,3'-T_2$ comprises quantitating as little as 4.0 pg/mL (7.6 pmol/L). In one embodiment, the quantitation limit for $3,3'-T_2$ in the test sample is 4.0 pg/mL (7.6 pmol/L).

In one embodiment, the determining the test sample $T_3$ comprises detecting as little as 1.5 pg/mL (2.3 pmol/L). In one embodiment, the detection limit for $T_3$ in the test sample is 1.5 pg/mL (2.3 pmol/L).

In one embodiment, the determining the test sample $T_3$ comprises quantitating as little as 3.0 pg/mL (4.6 pmol/L). In one embodiment, the quantitation limit for $T_3$ in the test sample is 3.0 pg/mL (4.6 pmol/L).

In one embodiment, the determining the test sample $T_4$ comprises detecting as little as 1.0 pg/mL (1.3 pmol/L). In one embodiment, the detection limit for $T_4$ in the test sample is 1.0 pg/mL (1.3 pmol/L).

In one embodiment, the determining the test sample $T_4$ comprises quantitating as little as 1.8 pg/mL (2.3 pmol/L). In one embodiment, the quantitation limit for $T_4$ in the test sample is 1.8 pg/mL (2.3 pmol/L).

DETAILED DESCRIPTION OF THE INVENTION

Figure 1:
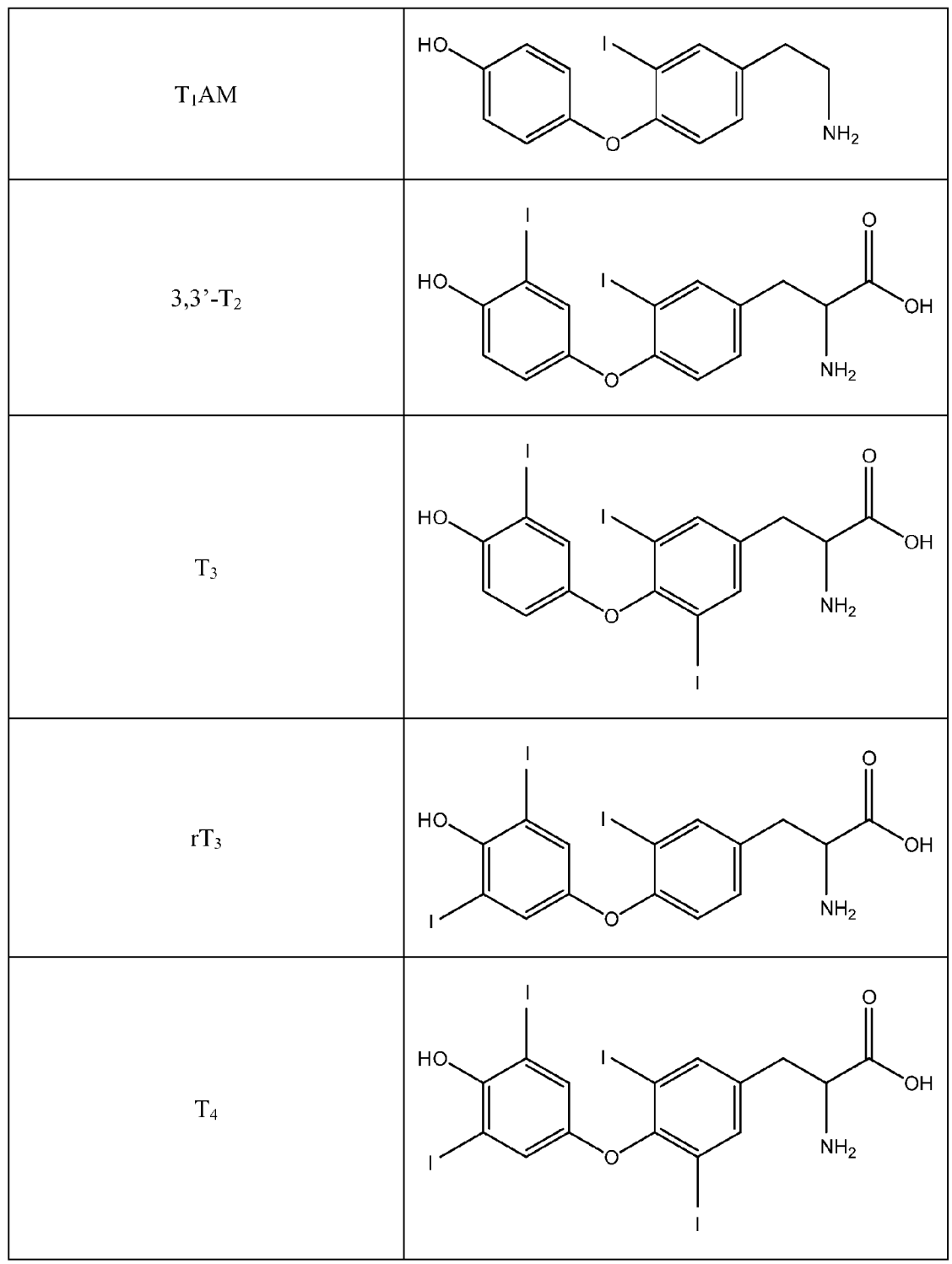
FIG. 1 depicts structural formulas of $3,3'-T_2$, $T_3$, $rT_3$, $T_4$, and $T_1AM$.

The thyroid gland synthesizes $T_4$ and $T_3$ through iodination of tyrosine residues in thryoglobulin, a glycoprotein of approximately 650 kDa molecular weight that is synthesized in follicular cells of the thyroid gland. Resulting mono- and di-iodotyrosines undergo oxidative condensation to yield a variety of iodothyronines, including $T_4$ and $T_3$, still associated with thyroglobulin. Upon hydrolysis within follicular cell phagolysosomes, free $T_4$ and $T_3$ are released into the circulation. While essentially all $T_4$ is so derived, only about 20 percent of $T_3$ originates in the thyroid, the remainder being generated in extraglandular tissues by enzymatic removal of the 5' iodine from the outer ring of $T_4$. In addition to $T_3$, $rT_3$, $3,3'-T_2$, and $T_1AM$ are also generated in extraglandular tissues by enzymatic processing.

In the blood, $T_4$ and $T_3$ are almost entirely bound to plasma proteins. These proteins include thyroxine binding protein (TBG), prealbumin, and albumin, among others. In pregnancy there is an increase in circulating immunoglobulins, which may also bind to $T_4$ and $T_3$. However, only uncomplexed $T_4$ and $T_3$, referred to as free $T_4$ and free $T_3$, respectively, are available to tissues. Because $T_3$ is bound less tightly to proteins than $T_4$, the normal proportion of free $T_3$ is about an order of magnitude greater than that of free $T_4$.

An aspect of the invention is a method of simultaneously assaying thyroxine ($T_4$), triiodothyronine ($T_3$), 3,3'-diiodo-L-thyronine ($3,3'-T_2$), and 3-iodothyronamine ($T_1AM$).

The method includes the steps of:

a) providing a test sample, wherein the test sample comprises $T_4$, $T_3$, $3,3'-T_2$, and $T_1AM$;

b) providing a calibration sample, wherein the calibration sample comprises known quantities of reference $T_4$, $T_3$, $3,3'-T_2$, and $T_1AM$;

c) combining the test sample with the calibration sample;

d) determining by mass spectrometry the quantity of $T_4$, $T_3$, $3,3'-T_2$, and $T_1AM$ in the test sample and the quantity of the reference $T_4$, $T_3$, $3,3'-T_2$, and $T_1AM$; and e) calibrating the quantity of the $T_4$, $T_3$, $3,3'-T_2$, and $T_1AM$ in the test sample against the known and determined quantities of the reference $T_4$, $T_3$, $3,3'-T_2$, and $T_1AM$ in the calibration sample.

In one embodiment the invention is a method of simultaneously assaying $T_4$, $T_3$, $3,3'-T_2$, $T_1AM$, and reverse $T_3$ ($rT_3$). The method includes the steps of:

a) providing a test sample, wherein the test sample comprises $T_4$, $T_3$, $rT_3$, $3,3'-T_2$, and $T_1AM$;

b) providing a calibration sample, wherein the calibration sample comprises known quantities of reference $T_4$, $T_3$, $rT_3$, $3,3'-T_2$, and $T_1AM$;

c) combining the test sample with the calibration sample;

d) determining by mass spectrometry the quantity of $T_4$, $T_3$, $rT_3$, $3,3'-T_2$, and $T_1AM$ in the test sample and the quantity of the reference $T_4$, $T_3$, $rT_3$, $3,3'-T_2$, and $T_1AM$; and e) calibrating the quantity of the $T_4$, $T_3$, $rT_3$, $3,3'-T_2$, and $T_1AM$ in the test sample against the known and determined quantities of the reference $T_4$, $T_3$, $rT_3$, $3,3'-T_2$, and $T_1AM$ in the calibration sample.

Test Samples

Suitable test samples include any test sample that may contain an analyte of interest. In some embodiments, a sample is a biological sample; that is, a sample obtained from any biological source, such as an animal, a cell culture, an organ culture, etc. In certain embodiments, samples are obtained from a mammalian animal, such as a dog, cat, horse, etc. Exemplary mammalian animals are primates, including humans. In one embodiment, the sample is obtained from a human. Exemplary samples include blood, plasma, serum, hair, muscle, urine, saliva, tear, cerebrospinal fluid, amniotic fluid, or other tissue sample. In one embodiment, the sample is obtained from blood, plasma, serum, amniotic fluid, or cerebrospinal fluid. Such samples may be obtained, for example, from a patient; that is, a living person presenting oneself in a clinical setting for diagnosis, prognosis, or treatment of a disease or condition.

Calibration Samples

In certain embodiments, the term "calibration sample" refers to a sample which comprises a known quantity of one or more analytes. The term "known quantity" means that the absolute quantity, or a qualitative quantity of the analyte or analytes in each aliquot of the calibration sample is known. A qualitative quantity in the present context means a quantity which is not known absolutely, but may be a range of quantities that are expected in a subject having a particular state, for example a subject in a healthy or diseased state, or some other expected range depending on the type of test sample under investigation.

In most methods according to the invention, the quantity of an analyte in the calibration sample is a known absolute quantity. This allows for the absolute quantity of an analyte in a test sample to be determined in various methods of the invention.

In one embodiment, the same calibration sample can be used for each test sample to be assayed.

In certain embodiments, the calibration sample comprises a known quantity of an analyte, wherein the analyte in the calibration sample is differentially labeled with one or more mass spectrometrically distinct groups (i.e., the analyte in the calibration sample is a "reference analyte"), such that the analyte in the test sample and the analyte in the calibration sample can be distinguished by mass spectrometry. In certain embodiments, the analyte in the calibration sample, or the reference analyte, may be any one or any combination of radioisotopically labeled $T_4$, $T_3$, $3,3'$-$T_2$, $T_1AM$, and $rT_3$. In one embodiment, the analytes in the calibration sample, or the reference analytes, are a combination of radioisotopically labeled $T_4$, $T_3$, $3,3'$-$T_2$, and $T_1AM$. In one embodiment, the analytes in the calibration sample, or the reference analytes, are a combination of radioisotopically labeled $T_4$, $T_3$, $3,3'$-$T_2$, $T_1AM$, and $rT_3$. In certain embodiments, a reference analyte is selected from the group consisting of deuterated $T_4$, $T_3$, $3,3'$-$T_2$, $T_1AM$, and $rT_3$. In certain embodiments, a reference analyte is selected from the group consisting of $^{13}C$-labeled $T_4$, $T_3$, $3,3'$-$T_2$, $T_1AM$, and $rT_3$. In certain embodiments, a reference analyte is selected from the group consisting of deuterated $T_4$, $T_3$, $3,3'$-$T_2$, $T_1AM$, and $rT_3$, and $^{13}C$-labeled $T_4$, $T_3$, $3,3'$-$T_2$, $T_1AM$, and $rT_3$. In one embodiment, the reference $T_4$ is deuterium-labeled $T_4$. In one embodiment, the reference $T_3$ is $^{13}C$-labeled $T_3$. In one embodiment, the reference $3,3'$-$T_2$ is $^{13}C$-labeled $3,3'$-$T_2$. In one embodiment, the reference $T_1AM$ is deuterium-labeled $T_1AM$. In one embodiment, the reference $rT_3$ is deuterium-labeled $rT_3$. In one embodiment, the reference $rT_3$ is $^{13}C$-labeled $rT_3$. In certain embodiments, the calibration sample comprises a known quantity of the analyte, wherein the analyte in the calibration sample is the same as the analyte in the test sample. In certain embodiments, the reference analytes are spiked into the sample of interest at a defined concentration and used as an internal standard.

In certain embodiments, the calibration sample may comprise a normal quantity of an analyte or plurality of analytes. In certain embodiments, the quantity of the analyte or analytes in the calibration sample may indicative of a healthy animal, e.g., a human. In certain embodiments, the calibration sample may comprise an analyte or plurality of analytes in a quantity or quantities indicative of the presence and/or stage of a particular disease. In certain embodiments, the calibration sample comprises an analyte or plurality of analytes in a quantity or quantities indicative of the efficacy and/or toxicity of a therapy. Standard panels of known markers of a particular trait, such as presence and/or stage of disease, response to therapy, and/or toxicity, may be prepared. In certain embodiments, calibration samples comprising body fluids or tissue extracts could be prepared from patients with well-characterized disease or condition, including but not limited to hypertension, congestive heart failure, diabetes mellitus, pregnancy, and attention deficit disorder. In certain embodiments, known amounts of such samples are added to multiple test samples in such a manner that, for a series of analytes, ion intensities in the MS/MS scan can be normalized based on the ion intensity of the common calibration sample, thereby providing more accurate comparisons between the separate analytes, reducing the analytical variability of the study.

Sample Preparation for Mass Spectrometry

Methods may be used prior to mass spectrometry to enrich thyroxine, thyronines, and/or thyronamines relative to other components in the sample, or to increase the concentration of the thyroxine, thyronines, and/or thyronamines in the combined sample. Such methods include, for example, filtration, centrifugation, thin layer chromatography (TLC), electrophoresis including capillary electrophoresis, affinity separations including immunoaffinity separations, extraction methods including ethyl acetate extraction and methanol extraction, and the use of chaotropic agents or any combination of the above or the like.

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, extraction, precipitation, centrifugation, delipidization, dilution, combinations thereof and the like.

Protein precipitation (i.e., deproteination) is one method of preparing a liquid biological sample, such as serum or plasma, for chromatography. Such protein precipitation methods are well known in the art, for example, Polson et al., J Chromatography B 785:263-275 (2003), describes protein precipitation methods suitable for use in the methods of the invention. Protein precipitation may be used to remove most of the protein from the sample leaving thyroxine and thyronines soluble in the supernatant. The samples can be centrifuged to separate the liquid supernatant from the precipitated proteins. The resultant supernatant can then be applied to liquid chromatography and subsequent mass spectrometry analysis.

In one embodiment of the invention, the protein precipitation involves adding one volume of the liquid sample (e.g., plasma) to about four volumes of methanol. In another embodiment, the protein precipitation involves adding two volumes of liquid sample (e.g., plasma) to about three volumes of methanol. In certain embodiments of protein precipitation, the methanol solution contains an internal standard and/or the adduct. In certain embodiments, the use of protein precipitation obviates the need for high turbulence liquid chromatography ("HTLC") or on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography ("HTLC").

Ultrafiltration, a variety of membrane filtration used in industry and research for purifying and concentrating macromolecular solutions, may be used to prepare the samples for mass spectrometry. In certain embodiments, ultrafiltration is used to remove high-molecular weight molecules from a sample. In certain embodiments, ultrafiltration is used to remove molecules having a molecular weight above about 30 kDa from a sample. In certain embodiments, ultrafiltration at about 37° C. (human physiological temperature) is used to remove molecules having a molecular weight above about 30 kDa from a sample. In certain embodiments, ultrafiltration may be applied in cross-flow or dead-end mode and separation in ultrafiltration undergoes concentration polarization. In certain embodiments, ultrafiltration yields free iodothyronines and/or thyronamines. In certain embodiments, carrying out ultrafiltration prior to MS, while it may make the quantification process slightly less efficient, is desirable because of the ability to obtain a measurement of the free iodothyronines and/or thyronamines.

Liquid Chromatography

Generally, chromatography may be performed prior to mass spectrometry; the chromatography may be liquid chromatography, such as high performance liquid chromatography (HPLC).

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

As used herein, the term "gas chromatography" refers to chromatography in which the sample mixture is vaporized and injected into a stream of carrier gas (such as nitrogen or helium) moving through a column containing a stationary phase composed of a liquid or a particulate solid and is separated into its component compounds according to the affinity of the compounds for the stationary phase.

Liquid chromatography (LC) including high-performance liquid chromatography (HPLC) rely on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process. HPLC has been successfully applied to the separation of compounds in biological samples.

Various methods have been described involving the use of HPLC for sample clean-up prior to mass spectrometry analysis. See, e.g., Taylor et al., Therapeutic Drug Monitoring 22:608-12 (2000) (manual precipitation of blood samples, followed by manual C18 solid phase extraction, injection into an HPLC for chromatography on a C18 analytical column, and MS/MS analysis); and Salm et al., Clin. Therapeutics 22 Supl. B:B71-B85 (2000) (manual precipitation of blood samples, followed by manual CIS solid phase extraction, injection into an HPLC for chromatography on a C18 analytical column, and MS/MS analysis).

One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In one embodiment, the sample (or pre-purified sample) is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e., mixed) mode. During chromatography, the separation of materials is effected by variables such as choice of eluent (also known as a "mobile phase"), choice of gradient elution and the gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

Recently, high turbulence liquid chromatography ("HTLC"), also called high throughput liquid chromatography, has been applied for sample preparation prior to analysis by mass spectrometry. See, e.g., Zimmer et al., J. Chromatogr. A 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, HTLC, alone or in combination with one or more purification methods, may be used to purify the sample prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. In certain embodiments of the method, samples are subjected to protein precipitation as described above prior to loading on the HTLC column; in alternative embodiments, the samples may be loaded directly onto the HTLC without being subjected to protein precipitation.

Detection and Quantization by Mass Spectrometry

Disclosed are mass spectrometric methods for detecting the presence or amount of thyroxine, thyronines, and thyronamines in a sample. Mass spectrometry may be performed using a mass spectrometer which includes an ion source for ionizing the fractionated sample and creating charged molecules for further analysis. For example ionization of the sample may be performed by electrospray ionization (ESI), atmospheric pressure chemical ionization (APCI), atmospheric pressure photoionization (APPI), photoionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

As used herein, "mass spectrometry" (MS) refers to an analytical technique to identify compounds by their mass and charge. MS technology generally includes (1) ionizing the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector. See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based on Mass Spectrometry;" U.S. Pat. No. 6,124,137, entitled "Surface-Enhanced Photolabile Attachment and Release for Desorption and Detection of Analytes;" Wright et al., Prostate Cancer and Prostatic Diseases 2:264-76 (1999); and Merchant and Weinberger, Electrophoresis 21:1164-67 (2000).

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g., ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, or triethanolamine.

The term "field desorption" as used herein refers to methods in which a non-volatile test sample is placed on an ionization surface, and an intense electric field is used to generate analyte ions.

The term "ionization" as used herein refers to the process of generating an analyte ion having a net electrical charge equal to one or more electron units. Negative ions are those having a net negative charge of one or more electron units, while positive ions are those having a net positive charge of one or more electron units.

The term "operating in negative ion mode" refers to those mass spectrometry methods where negative ions are detected.

In one embodiment the mass spectrometry is performed operating in positive ion mode. The term "operating in positive ion mode" refers to those mass spectrometry methods where positive ions are detected.

The term "desorption" as used herein refers to the removal of an analyte from a surface and/or the entry of an analyte into a gaseous phase.

In certain embodiments, the following mass spectrometers can be used: any tandem-mass spectrometer, including quadrupole time-of-flight (QTOF), matrix assisted laser desorption/ionization time-of-flight (MALDI/TOF), hybrid quadrupole-linear ion trap mass spectrometers, and liquid chromatography-tandem mass spectrometers such as the API 2000™ mass spectrometer, the API 3000™ mass spectrometer, the API 4000™ mass spectrometer, or the API 5000™ mass spectrometer, such as those described in U.S. Pat. Nos. 4,121,099; 4,137,750; 4,328,420; 4,963,736; 5,179,278; 5,248,875; 5,412,208; and 5,847,386 (Applied Biosystems/MDS SCIEX, Foster City, Calif./Concord Ontario, Canada).

After the sample has been ionized, the positively charged or negatively charged ions thereby created may be analyzed to determine a mass-to-charge ratio (i.e., m/z). Suitable analyzers for determining mass-to-charge ratios include quadrupole analyzers, ion trap analyzers, and time-of-flight analyzers. The ions may be detected using any of several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM). In one embodiment, the mass-to-charge ratio is determined using a quadrupole analyzer. For example, in a "quadrupole" or "quadrupole ion trap" instrument, ions in an oscillating radio frequency field experience a force proportional to the direct current (DC) potential applied between electrodes, the amplitude of the radio frequency (RF) signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One may enhance the resolution of the MS technique by employing "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas to produce the daughter ions. Because both the precursor and fragment ions are produced in a reproducible fashion under a given set of ionization/fragmentation conditions, the MS/MS technique can provide an extremely powerful analytical tool. For example, the combination of filtration fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole ($10^{-15}$ mole) levels in very short ion pulses. Mass spectrometers that combine time-of-flight analyzers with tandem MS are also well known to the artisan. Additionally, multiple mass spectrometry steps can be combined in methods known as "MS/MS$_n$." Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 100 to 2000 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule.

In certain embodiments, an internal standard is used to generate a standard curve for calculating the quantity of the thyroxine, thyronine, or thyronamine. Methods of generating and using such standard curves are well known in the art and one of ordinary skill is capable of selecting an appropriate internal standard. For example, an isotope of a thyroxine may be used as an internal standard, such as a deuterium-labeled thyroxine. Numerous other methods for relating the presence or amount of an ion to the presence or amount of the original molecule will be well known to those of ordinary skill in the art.

One or more steps of the methods of the invention can be performed using automated machines. In certain embodiments, one or more purification steps are performed on line, and more preferably all of the purification and mass spectrometry steps may be performed in an on-line fashion.

In certain embodiments, such as MS/MS, where precursor ions are isolated for further fragmentation, collision activation dissociation (CAD) is often used to generate the fragment ions for further detection. In CAD, precursor ions gain energy through collisions with an inert gas, and subsequently fragment by a process referred to as "unimolecular decomposition". Sufficient energy must be deposited in the precursor ion so that certain bonds within the ion can be broken due to increased vibrational energy.

In certain embodiments thyroxine, thyronine, and/or thyronamine is detected and/or quantified using LC-MS/MS as follows. The samples are subjected to liquid chromatography, preferably HPLC, the flow of liquid solvent from the chromatographic column enters the heated nebulizer interface of a LC-MS/MS analyzer and the solvent/analyte mixture is converted to vapor in the heated tubing of the interface. The analytes (i.e., thyroxine, thyronines, and/or thyronamines) contained in the nebulized solvent are ionized by the corona discharge needle of the interface, which applies a large voltage to the nebulized solvent/analyte mixture. The ions, i.e., precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass-to-charge ratios of the thyroxine, thyronines, and/or thyronamines to be analyzed. Precursor ions with the correct m/z ratios of the precursor ions of thyroxine, thyronines, and/or thyronamines are allowed to pass into the collision chamber (Q2), while unwanted ions with any other m/z collide with the sides of the quadrupole and are eliminated. Precursor ions entering Q2 collide with neutral Argon gas molecules and fragment. This process is called Collision Activated Dissociation (CAD). The fragment ions generated are passed into quadrupole 3 (Q3), where the fragment ions of thyroxine, thyronines, and/or thyronamines are selected while other ions are eliminated.

The methods of the invention may involve MS/MS performed in either positive or negative ion mode. In one embodiment the MS/MS performed in positive ion mode. Using standard methods well known in the art, one of ordinary skill is capable of identifying one or more fragment ions of MS/MS performed in either positive or negative ion mode that can be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (thyroxine, thyronine, or thyronamine) of interest. In certain embodiments, the area under the curves, or amplitude of the peaks, for fragment ion(s) and/or precursor ions are measured to determine the amount of thyroxine, thyronines, and/or thyronamines. As described above, the relative abundance of a given ion can be converted into an absolute amount of the original analyte, i.e., thyroxine, thyronines, and/or thyronamines, using calibration standard curves based on peaks of one or more ions of an internal molecular standard.

In certain aspects of the invention, the quantity of various ions is determined by measuring the area under the curve or the amplitude of the peak and a ratio of the quantities of the ions is calculated and monitored (i.e., "daughter ion ratio monitoring"). In certain embodiments of the method, the ratio(s) of the quantity of a precursor ion and the quantity of one or more fragment ions of thyroxine, thyronines, and/or thyronamines can be calculated and compared to the ratio(s) of a molecular standard of the thyroxine, thyronines, and/or thyronamines similarly measured. In embodiments where more than one fragment ion of a thyroxine, thyronine, or thyronamine is monitored, the ratio(s) for different fragment ions may be determined instead of, or in addition to, the ratio of the fragment ion(s) compared to the precursor ion. In embodiments where such ratios are monitored, if there is a substantial difference in an ion ratio in the sample as compared to the molecular standard, it is likely that a molecule in the sample is interfering with the results. To the contrary, if the ion ratios in the sample and the molecular standard are similar, then there is increased confidence that there is no interference. Accordingly, monitoring such ratios in the samples and comparing the ratios to those of authentic molecular standards may be used to increase the accuracy of the method.

As described herein, the presence or absence or amount of a plurality of analytes in a sample can be detected in a single assay using the above described MS/MS methods.

The term "detection limit", or equivalently "lower limit of detection", as used herein, refers to a minimum concentration of an analyte capable of detection using a method of the invention.

The term "quantitation limit", or equivalently "lower limit of quantitation", as used herein, refers to a minimum concentration of an analyte capable of quantitative measurement using a method of the invention. For example, a quantitation limit may be expressed as a numerical value within a certain confidence interval. While the detection limit and the quantitation limit may be identical for any given analyte, it is not unusual for the detection limit to be lower than the quantitation limit.

Isotope Dilution Tandem Mass Spectrometry

Quantification using spiking with isotopically labeled compounds (the isotope dilution method) has helped to generate many valuable contributions to science. The approach relies on linearity of signal versus molecular concentration and reproducibility of sample processing. Specifically, isotope dilution tandem mass spectrometry incorporates additional dilution steps that act as an internal calibration so that an independent isotopic reference material is not required. It avoids the need to measure the isotope ratio of the highly enriched spike directly, and enables the final results to be arranged as a combination of measurements that are largely insensitive to instrument bias and drift. Consequently, it has the potential to extend the scope of application of isotope dilution tandem mass spectrometry to include analysis for which reference materials with certified isotope ratios are not available or where contamination of the instrument by the highly enriched spike causes difficulty.

The use of isotope dilution tandem mass spectrometry for the analysis of thyroid hormones has been described in U.S. Pat. No. 7,618,827, which is hereby incorporated by reference. Further methods for simultaneously measuring iodothyronines using LC/MS/MS within a single run have been reported. See, for example, Gu, J., O. P. Soldin, and S. J. Soldin, Simultaneous quantification of free triiodothyronine and free thyroxine by isotope dilution tandem mass spectrometry. Clin Biochem, 40(18):1386-91 (2007); Soldin, S. J., et al., The measurement of free thyroxine by isotope dilution tandem mass spectrometry. Clin Chim Acta, 358(1-2):113-8 ((2005); Soukhova, N., O. P. Soldin, and S. J. Soldin, Isotope dilution tandem mass spectrometric method for $T_4/T_3$. Clin Chim Acta, 343(1-2):185-90 (2004); Soldin, O. P., D. M. Mendu, and S. J. Soldin, Development of a method for the simultaneous measurement of stable isotope C13- and C12- thyroxine in human serum or plasma. Thyroid, 18(1):S-85 (2008); and Soldin, O. P., J. Gu, and S. J. Soldin, Thyronamines: Tandem mass spectrometry quantification in biological fluids. Thyroid, 19(s1):S-100-S-116 (2009).

Because isotopes of the same element have the same chemical characteristics and therefore behave almost identically, their mass differences, due to a difference in the number of neutrons, result in fractionation and thus are quantifiable using the highly sensitive methods disclosed herein.

EXAMPLES

The invention now being generally described, it will be more readily understood by reference to the following, which is included merely for purposes of illustration of certain aspects and embodiments of the present invention, and is not intended to limit the invention.

Chemicals and Reagents

Unlabeled 3-iodothyronamine ($T_1AM$) and 3,3'-diiodo-L-thyronine (3,3'-$T_2$); deuterium-labeled 3-iodothyronamine ($T_1AM$-$d_4$) and L-thyroxine ($T_4$-$d_5$): L-thyroxine-[tyrosine $^2H_5$]; and $^{13}C$-labeled 3,3'-diiodo-L-thyronine (3,3'-$T_2$-$^{13}C_6$): 3,3'-diiodo-L-thyronine-[outer ring-$^{13}C_6$] and 3,3',5-triiodo-L-thyronine ($T_3$-$^{13}C_6$): 3,3',5-triiodo-L-thyronine-[L-tyrosine ring-$^{13}C_6$] were all obtained from IsoSciences (King of Prussia, Pa.). Unlabeled 3,3',5-triiodo-L-thyronine ($T_3$) was purchased from Fluka (Buchs, Switzerland). Unlabeled L-thyroxine ($T_4$) was purchased from Sigma (St. Louis, Mo.). For $rT_3$, the labeled form may be deuterium-labeled or $^{13}C$-lableled. HPLC grade methanol, formic acid, and ammonium hydroxide were obtained from Fisher Scientific (Fair Lawn, N.J.). Distilled de-ionized water was prepared from Millipore AFS-8D and Synergy UV ultrapure water systems (Billerica, Mass.).

Preparation of Internal Standards, Calibration Standards, and in House Controls

Stock solutions of each analyte and internal standard were prepared separately to obtain a concentration of 1 mg/mL for each. 40% ammonium hydroxide (v/v) in methanol was used as a solvent except that methanol alone was used for dissolving 3,3'-$T_2$ and its internal standard 3,3'-$T_2$-$^{13}C_6$. The stock solutions were diluted with appropriate amounts of methanol, respectively, to obtain spiking solutions. The solutions were stored at −20° C. and were stable for at least 6 months. Standards for the calibration curve in the range of 2.5-1000 pg/mL (7.0-2815.5 pmol/L) for 3-iodothyronamine ($T_1AM$), 2.5-1000 pg/mL (4.8-1905.5 pmol/L) for 3,3'-$T_2$, 2.5-1000 ng/dL (0.038-15.4 nmol/L) for $T_3$, and 0.05-20 µg/dL (0.64-257.4 nmol/L) for $T_4$ were prepared by adding spiking solutions to 3% human gamma (γ)-globulin (volume of spiking solution <2% of final volume). In-house quality control solutions at three concentration levels (low, medium, and high) were prepared in the same way to evaluate within-day and between-day precision as well as the accuracy of the method. A diluted solution containing 300 pg/mL (835.2 pmol/L) $T_1AM$-$d_4$, 300 pg/mL (565.2 pmol/L) 3,3'-$T_2$-$^{13}C_6$, 150 ng/dL (2.3 nmol/L) $T_3$-$^{13}C_6$, and 1 µg/dL (12.8 nmol/L) $T_4$-$d_5$ in acetonitrile was used as working internal standard solution.

Sample Preparation

Twenty human serum/plasma samples of normal controls were obtained in studies approved by the hospital Institutional Review Board (IRB). All samples were kept at −80° C. until analysis. Samples were thawed at room temperature before use. To a 1.5 mL conical plastic Eppendorf centrifuge tube, 200 µL of calibration standard, quality control, or human plasma/serum sample was added and deproteinized with 200 µL of internal standard solution. The tube was capped, vortex-mixed vigorously for 30 s, and centrifuged for 10 min at 13,000 rpm. After centrifugation, 250 µL of supernatant was diluted with 250 µL of distilled de-ionized water and a 250 µL aliquot was injected into the LC-MS/MS system.

Instrumentation

An API-5000 tandem mass spectrometer (Applied Biosystems/MDS SCIEX, Foster City, Calif./Concord, Ontario, Canada) equipped with TurbolonSpray source was employed in the positive ion multiple reaction monitoring mode to perform the analysis. The HPLC system consisted of three Shimadzu LC-20AD pumps, a Shimadzu SIL-HT$_A$ autosampler, and a Shimadzu DGU-20A$_5$ degasser (Shimadzu Scientific Instruments, Columbia, Md.). Quantification by multiple reaction-monitoring (MRM) analysis was performed in the positive mode. Transitions to be monitored and compound-dependent parameters are summarized in Table 1.

TABLE 1

MRM conditions in positive ion mode

| Compound | MRM transition | Declustering potential | Entrance potential | Collision energy | Collision cell exit potential |
|---|---|---|---|---|---|
| $T_1AM$ | 356.1/212.0 | 86 | 10 | 29 | 12 |
| $T_1AM$-$d_4$ | 360.1/216.1 | 86 | 10 | 27 | 8 |
| 3,3'-$T_2$ | 525.9/480.0 | 141 | 10 | 29 | 10 |
| 3,3'-$T_2$-$^{13}C_6$ | 531.9/485.9 | 116 | 10 | 29 | 22 |

TABLE 1-continued

MRM conditions in positive ion mode

| Compound | MRM transition | Declustering potential | Entrance potential | Collision energy | Collision cell exit potential |
|---|---|---|---|---|---|
| $T_3$ | 651.8/605.8 | 171 | 10 | 29 | 26 |
| $T_3$-$^{13}C_6$ | 657.8/611.7 | 16 | 10 | 33 | 26 |
| $T_4$ | 777.7/731.5 | 231 | 10 | 35 | 30 |
| $T_4$-$d_5$ | 782.7/736.5 | 61 | 10 | 35 | 30 |

Compound-dependent and instrument-dependent parameters were optimized for each analyte by infusion of 100 ng/mL standard solutions in methanol at 10 µL/min. Nitrogen served as auxiliary, curtain, and collision gas. The main working parameters of the mass spectrometer were: collision gas 9, curtain gas 35, nebulizer gas 50, turbo gas 50, ionspray voltage 5500 V, probe temperature 650° C., and dwell time 200 msec. Data were acquired and processed by Analyst 1.4.2 software package (Applied Biosystems/MDS SCIEX).

LC/MS/MS Procedure

The procedure involves an online extraction/cleaning of the injected samples followed by sample introduction into the mass spectrometer by activating a built-in Valco switching valve. 250 µL of the prepared sample was injected onto an Agilent Zorbox SB-C18 (2.1×30 mm, 1.8-micron) chromatographic column, where it underwent cleaning with 2% (v/v) methanol in 0.01% formic acid at a flow rate of 0.25 mL/min. After a 5 min wash, the switching valve was activated and the analytes of interest were eluted from the column with a water/methanol gradient at a flow rate of 0.25 mL/min and then introduced into the mass spectrometer. The gradient parameters are listed in Table 2.

TABLE 2

Gradient parameters

| | Time, min | Solvent C, % | |
|---|---|---|---|
| Cleaning | 0.00 | 100 | |
| | 5.00 | 100 | |
| | Time, min | Solvent A, % | Solvent B, % |
| Elution | 5.01 | 35 | 65 |
| | 8.00 | 35 | 65 |
| | 9.00 | 0 | 100 |
| | 9.90 | 0 | 100 |
| | 10.00 | 100 | 0 |

Solvent A: 2% (v/v) methanol/water in 0.01% formic acid
Solvent B: 98% (v/v) methanol/water in 0.01% formic acid
Solvent C: 2% (v/v) methanol/water in 0.01% formic acid, was used to wash the column between 0.00-5.00 min Accuracy and Precision The accuracy of this method was evaluated by performing recovery studies. The between-day and within-day precision was assessed by analyzing in-house quality control samples at three different concentrations in replicates for $T_1AM$, 3,3'-$T_2$, $T_3$, and $T_4$. The between-day precision was measured on 10 different days.

Results

Figure 2:
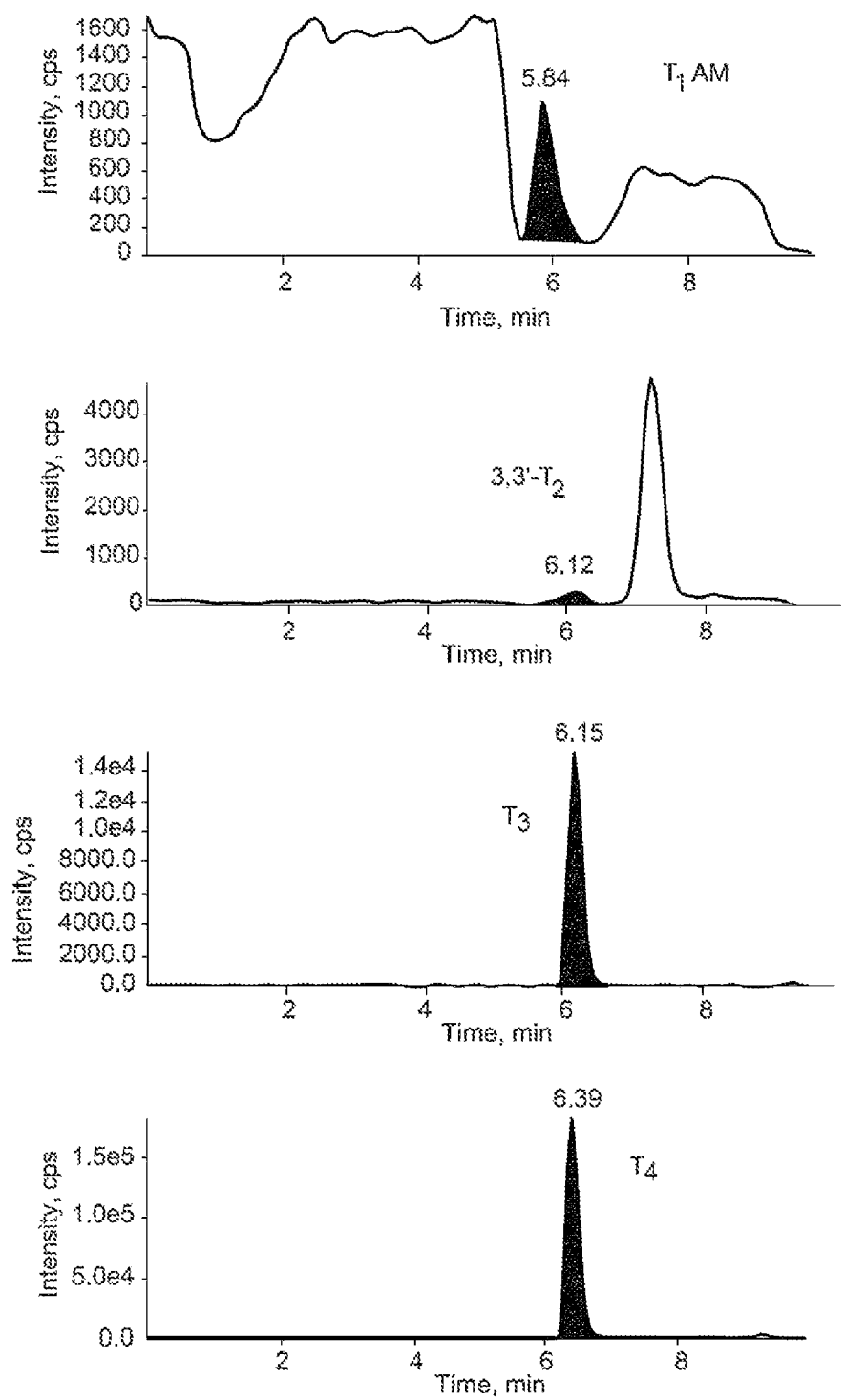
FIG. 2 depicts tandem mass spectrometric chromatograms obtained from serum of a pregnant patient. The concentrations found were: $T_1AM$ [96.4 pg/mL (271.4 pmol/L)], $3,3'-T_2$ [47.3 pg/mL (90.1 pmol/L)], $T_3$ [93.2 ng/dL (1.4 nmol/L)], and $T_4$ [10.5 µg/dL (135.2 nmol/L)].

The high sensitivity and specificity obtained by employing an API-5000 tandem mass spectrometer enabled us to quantify all of these analytes at the picomolar level. Analysis by tandem mass spectrometry in the positive mode showed eight major parent ions, 356.1, 360.1, 525.9, 531.9, 651.8, 657.8, 777.7, and 782.7 m/z, which respectively correspond to the $[M+H]^+$ ions of $T_1AM$, $T_1AM$-$d_4$, 3,3'-$T_2$, 3,3'-$T_2$-$^{13}C_6$, $T_3$, $T_3$-$^{13}C_6$, $T_4$, and $T_4$-$d_5$. For $T_1AM$, the product ion of 339.0 m/z $[M+H-NH_3]^+$, was significantly observed by the loss of ammonia from its parent ion. But the MS/MS was not too selective to distinguish the interfering peaks from the target analyte peak in the serum samples. Therefore the second product ion of 212.0 m/z $[M+H-NH_3-I]^+$, which corresponds to the iodide loss from the first product ion, was used for the measurement of $T_1AM$. For thyronines like 3,3'-$T_2$, $T_3$, $T_4$, and their corresponding isotopic compounds, the product ions $[M+H-HCOOH]^+$, were obtained by a loss of a formyl moiety from the parent ions. These were along the lines of previously reported studies [1,5,20]. Detailed information about transitions to be monitored are summarized in Table 1. Using isotopic internal standards overcame the potential problem of ion suppression. The optimized chromatographic conditions (Table 2) made it possible to measure simultaneously $T_1AM$, 3,3'-$T_2$, $T_3$, and $T_4$ within 10 minutes. Chromatograms of all analytes obtained from serum of a pregnant patient are shown in FIG. 2.

Using the methods of the invention, reference ranges of 3,3'-$T_2$, $T_3$, $rT_3$, and $T_4$ were determined to be as shown in Table 3.

TABLE 3

Reference ranges of 3,3'-$T_2$, $T_3$, $rT_3$, and $T_4$.

| | | | Percentile | | Gaussian | | Hoffmann | |
|---|---|---|---|---|---|---|---|---|
| | | Units | 2.5th | 97.5th | 2.5th | 97.5th | 2.5th | 97.5th |
| $T_2$ | Male | pg/mL | 9.4 | 30.6 | 7.0 | 30.8 | 11.2 | 26.6 |
| | Female | pg/mL | 7.2 | 24.4 | 6.7 | 22.6 | 9.6 | 19.7 |
| $T_3$ | Male | ng/dL | 86.5 | 168.5 | 83.1 | 171.2 | 94.4 | 151.4 |
| | Female | ng/dL | 79.8 | 187.0 | 74.0 | 167.7 | 87.1 | 144.5 |
| $rT_3$ | Male | ng/dL | 8.8 | 23.1 | 8.5 | 24.4 | 11.3 | 21.5 |
| | Female | ng/dL | 9.5 | 25.1 | 7.7 | 23.1 | 10.5 | 20.3 |
| $T_4$ | Male | µg/dL | 4.9 | 10.5 | 4.7 | 10.2 | 5.6 | 9.2 |
| | Female | µg/dL | 5.1 | 11.3 | 4.2 | 10.9 | 5.4 | 9.6 |

The values shown in Table 3 were obtained from 130 normal, nonpregnant females aged 20-60y and 130 normal males aged 20-60y. $T_1AM$ reference intervals are not included in the table above because they were below the lower limit of quantitation. Based on results using the instant invention, $T_1AM$ reference intervals were below 5 pg/mL for both males and females.

Recovery studies for all of the analytes are shown in Table 4.

TABLE 4

Recovery study

| Test | Control | Replicates (n) | Target value (pg/mL) | Measured mean (pg/mL) | Recovery (%) |
|---|---|---|---|---|---|
| $T_1AM$ | 1 | 10 | 5 | 5.21 | 104.2 |
|  | 2 | 10 | 50 | 49.53 | 99.1 |
|  | 3 | 10 | 500 | 489.50 | 97.9 |
| $3,3'\text{-}T_2$ | 1 | 10 | 5 | 4.97 | 99.4 |
|  | 2 | 10 | 50 | 50.36 | 100.7 |
|  | 3 | 10 | 500 | 503.60 | 100.7 |
| $T_3$ | 1 | 10 | 50 | 49.65 | 99.3 |
|  | 2 | 10 | 1,000 | 1,023.70 | 102.4 |
|  | 3 | 10 | 5,000 | 4,838.00 | 96.8 |
| $T_4$ | 1 | 10 | 1,000 | 1,020.00 | 102.0 |
|  | 2 | 10 | 20,000 | 20,890.00 | 104.5 |
|  | 3 | 10 | 100,000 | 99,810.00 | 99.8 |

Accuracy (% of weighed-in target concentration measured) ranged between 96.8% and 104.5% for all analytes. The within-day and between-day precision at three levels are shown in Table 5. For all the analytes, the within-day and between-day coefficients of variation were between 1.9%-8.7% and 2.7%-7.3%, respectively, at all concentrations tested. Good linearity was obtained within the concentration range of 2.5-1000 pg/mL (7.0-2815.5 pmol/L) for $T_1AM$, 2.5-1000 pg/mL (4.8-1905.5 pmol/L) for $3,3'\text{-}T_2$, 2.5-1000 ng/dL (0.038-15.4 nmol/L) for $T_3$, and 0.05-20 μg/dL (0.64-257.4 nmol/L) for $T_4$ (r>0.999). The lower limits of detection (LLOD) at a signal-to-noise ratio of ~3 were 2.5 pg/mL (7.0 pmol/L) for $T_1AM$, 2.5 pg/mL (4.8 pmol/L) for $3,3'\text{-}T_2$, 1.5 pg/mL (2.3 pmol/L) for $T_3$, and 1.0 pg/mL (1.3 pmol/L) for $T_4$. The lower limits of quantification (LLOQ) were 4.0 pg/mL (11.3 pmol/L) for $T_1AM$, 4.0 pg/mL (7.6 pmol/L) for $3,3'\text{-}T_2$, 3.0 pg/mL (4.6 pmol/L) for $T_3$, and 1.8 pg/mL (2.3 pmol/L) for $T_4$.

TABLE 5

Within-day and between-day precision

| | | Within-day | | | Between-day | | |
|---|---|---|---|---|---|---|---|
| Test | Control | Replicates (n) | Mean (pg/mL) | CV (%) | Replicates (n) | Mean (pg/mL) | CV (%) |
| $T_1AM$ | 1 | 10 | 5.21 | 5.5 | 10 | 4.97 | 7.3 |
|  | 2 | 10 | 99.65 | 2.4 | 10 | 101.18 | 3.9 |
|  | 3 | 10 | 489.50 | 2.9 | 10 | 495.60 | 3.1 |
| $3,3'\text{-}T_2$ | 1 | 10 | 4.97 | 8.7 | 10 | 5.11 | 5.1 |
|  | 2 | 10 | 98.64 | 1.9 | 10 | 98.73 | 4.8 |
|  | 3 | 10 | 503.60 | 2.6 | 10 | 493.70 | 2.9 |
| $T_3$ | 1 | 10 | 242.60 | 2.5 | 10 | 250.50 | 3.9 |
|  | 2 | 10 | 1,023.70 | 4.1 | 10 | 1,032.60 | 4.4 |
|  | 3 | 10 | 4,838.00 | 2.5 | 10 | 4,954.00 | 2.7 |
| $T_4$ | 1 | 10 | 5,010.00 | 2.9 | 10 | 5,100.00 | 5.6 |
|  | 2 | 10 | 20,890.00 | 2.5 | 10 | 21,170.00 | 4.3 |
|  | 3 | 10 | 99,810.00 | 2.8 | 10 | 100,370.00 | 4.3 |

The method was applied to measure the concentrations of $T_1AM$, $3,3'\text{-}T_2$, $T_3$, and $T_4$ in serum samples of 20 normal/controls. The results are illustrated in Table 6.

TABLE 6

Concentrations of $T_1AM$, $3,3'\text{-}T_2$, $T_3$, and $T_4$ in serum samples of 20 controls

| | $T_1AM$ | | $3,3'\text{-}T_2$ | | $T_3$ | | $T_4$ | |
|---|---|---|---|---|---|---|---|---|
| Controls | (pg/mL) | (pmol/L) | (pg/mL) | (pmol/L) | (ng/dL) | (nmol/L) | (μg/dL) | (nmol/L) |
| 1 | 27.4 | 77.1 | 12.1 | 23.1 | 73.1 | 1.1 | 7.5 | 96.5 |
| 2 | 26.4 | 74.3 | 9.4 | 17.9 | 95.4 | 1.5 | 9.8 | 126.1 |
| 3 | 32.9 | 92.6 | 26.5 | 50.5 | 83.2 | 1.3 | 8.3 | 106.8 |
| 4 | <2.5 | <7.0 | 31.2 | 59.5 | 102.0 | 1.6 | 9.5 | 122.3 |
| 5 | <2.5 | <7.0 | 25.6 | 48.8 | 61.2 | 0.9 | 7.1 | 91.4 |
| 6 | 7.5 | 21.1 | 29.7 | 56.6 | 72.1 | 1.1 | 7.7 | 99.1 |
| 7 | 22.5 | 63.3 | 30.5 | 58.1 | 109.0 | 1.7 | 12.0 | 154.5 |
| 8 | 21.4 | 60.3 | 23.8 | 45.4 | 60.9 | 0.9 | 7.2 | 92.7 |
| 9 | 13.5 | 38.0 | 40.6 | 77.4 | 78.0 | 1.2 | 7.3 | 94.0 |
| 10 | 10.1 | 28.4 | 26.4 | 50.3 | 112.0 | 1.7 | 9.1 | 117.1 |
| 11 | <2.5 | <7.0 | 34.2 | 65.2 | 101.0 | 1.6 | 8.0 | 103.0 |
| 12 | 11.4 | 32.1 | 32.2 | 61.4 | 60.1 | 0.9 | 5.4 | 69.5 |
| 13 | 18.4 | 51.8 | 33.6 | 64.0 | 100 | 1.5 | 8.8 | 113.3 |
| 14 | 26.3 | 74.0 | 24.7 | 47.1 | 83.7 | 1.3 | 7.3 | 94.0 |
| 15 | 10.1 | 28.4 | 18.5 | 35.3 | 61.5 | 0.9 | 7.3 | 94.0 |
| 16 | 28.8 | 81.1 | 27.7 | 52.8 | 74.5 | 1.1 | 6.4 | 82.4 |
| 17 | 4.6 | 13.0 | 22.6 | 43.1 | 77.2 | 1.2 | 7.4 | 95.3 |
| 18 | 10.4 | 29.3 | 26.5 | 50.5 | 67.3 | 1.0 | 5.6 | 72.1 |

TABLE 6-continued

Concentrations of $T_1AM$, $3,3'-T_2$, $T_3$, and $T_4$ in serum samples of 20 controls

| Controls | $T_1AM$ (pg/mL) | $T_1AM$ (pmol/L) | $3,3'-T_2$ (pg/mL) | $3,3'-T_2$ (pmol/L) | $T_3$ (ng/dL) | $T_3$ (nmol/L) | $T_4$ (µg/dL) | $T_4$ (nmol/L) |
|---|---|---|---|---|---|---|---|---|
| 19 | <2.5 | <7.0 | 22.7 | 43.3 | 86.7 | 1.3 | 7.1 | 91.4 |
| 20 | 5.2 | 14.6 | 16.8 | 32.0 | 67.1 | 1.0 | 7.2 | 92.7 |

Concentrations of TAM and $3,3'-T_2$ found in controls ranged between 0-32.9 pg/mL (0-92.6 pmol/L) and 9.4-40.6 pg/mL (17.9-77.4 pmol/L), respectively. The concentrations of $T_1AM$ measured are below the measurable range of the method previously reported by Piehl et al. [1]. The mean serum concentrations in these controls were 17.3±9.3 pg/mL (48.7±26.1 pmol/L) for TAM and 25.8±7.5 pg/mL (49.1±14.1 pmol/L) for $3,3'-T_2$. The results for $3,3'-T_2$ matched those of previously published paper well [21], which showed the mean serum concentration of $3,3'-T_2$ in 62 healthy controls was 46.6±20.0 pmol/L. Finally, the $T_4$ and $T_3$ results in the control group are very similar to results previously published by our group [19] using an earlier version of the tandem mass spectrometric procedure for measurement of $T_4$ and $T_3$.

REFERENCES

[1] Piehl S, Heberer T, Balizs G, Scanlan T S, Köhrle J. Development of a validated liquid chromatography/tandem mass spectrometry method for the distinction of thyronine and thyronamine constitutional isomers and for the identification of new deiodinase substrates. Rapid Commun Mass Spectrom 2008; 22(20):3286-96.

[2] Scanlan T S. Minireview: 3-Iodothyronamine (T1AM): a new player on the thyroid endocrine team. Endocrinology 2009; 150(3):1108-11.

[3] Soukhova N, Soldin O P, Soldin S J. Isotope dilution tandem mass spectrometric method for T4/T3. Clin Chim Acta 2004; 343(1-2):185-90.

[4] Lanni A, Moreno M, Lombardi A, Goglia F. Calorigenic effect of diiodothyronines in the rat. J Physiol 1996; 494 (3):831-37.

[5] Scanlan T S, Suchland K L, Hart M E, et al. 3-Iodothyronamine is an endogenous and rapid-acting derivative of thyroid hormone. Nat Med 2004; 10(6):638-42.

[6] Hart M E, Suchland K L, Miyakawa M, Bunzow J R, Grandy D K, Scanlan T S. Trace amine-associated receptor agonists: synthesis and evaluation of thyronamines and related analogues. J Med Chem 2006; 49 (3): 1101-12.

[7] Zucchi R, Chiellini G, Scanlan T S, Grandy D K. Trace amine-associated receptors and their ligands. Br J Pharmacol 2006; 149(8):967-78.

[8] Grandy D K, Neve K A. Trace amine-associated receptor 1-Family archetype or iconoclast? Pharmacol Ther 2007; 116(3):355-90.

[9] Regard J B, Kataoka H, Cano D A, et al. Probing cell type-specific functions of Gi in vivo identifies GPCR regulators of insulin secretion. J Clin Invest 2007; 117(12): 4034

[10] Chiellini G, Frascarelli S, Ghelardoni S, et al. Cardiac effects of 3-iodothyronamine: a new aminergic system modulating cardiac function. FASEB J 2007; 21(7):1597-608.

[11] Frascarelli S, Ghelardoni S, Chiellini G, et al. Cardiac effects of trace amines: pharmacological characterization of trace amine-associated receptors. Eur J Pharmacol 2008; 587(1-3):231-6.

[12] Braulke L J, Klingenspor M, DeBarber A, et al. 3-Iodothyronamine: a novel hormone controlling the balance between glucose and lipid utilisation. J Comp Physiol B 2008; 178(2):167-77.

[13] Zucchi R, Ghelardoni S, Chiellini G. Cardiac effects of thyronamines. Heart Fail Rev 2010; 15(2):171-6.

[14] Wang R, Nelson J C, Weiss R M, Wilcox R B. Accuracy of free thyroxine measurements across natural ranges of thyroxine binding to serum proteins. Thyroid 2000; 10(1): 31-9.

[15] Klee G G, Hay I D. Biochemical thyroid function testing. Mayo Clin Proc 1994; 69:469-70.

[16] Engler H, Staub J J, Althaus B, Ryff-deLeche A, Gerber H. Assessment of antithyroglobulin and antimicrosomal autoantibodies in patients with autoimmune thyroid disease: comparison of haemagglutination assay, enzyme-linked immunoassay and radioligand assay. Clin Chim Acta 1989; 179(3):251-63.

[17] De Brabandere V I, Hou P, Stockl D, Thienpont L M, De Leenheer A P. Isotope dilution-liquid chromatography/electrospray ionization-tandem mass spectrometry for the determination of serum thyroxine as a potential reference method. Rapid Commun Mass Spectrom 1998; 12(16): 1099-103.

[18] Tai S S, Bunk D M, White E 5th, Welch M J. Development and evaluation of a reference measurement procedure for the determination of total 3,3',5-triiodothyronine in human serum using isotope-dilution liquid chromatography-tandem mass spectrometry. Anal Chem 2004; 76(17): 5092-6.

[19] Soukhova N, Soldin O P, Soldin S J. Isotope dilution tandem mass spectrometric method for T4/T3. Clin Chim Acta 2004; 343(1-2):185-90.

[20] DeBarber A E, Geraci T, Colasurdo V P, Hackenmueller S A, Scanlan T S. Validation of a liquid chromatography-tandem mass spectrometry method to enable quantification of 3-iodothyronamine from serum. J Chromatogr A 2008; 1210(1):55-9.

[21] Pinna G, Hiedra L, Meinhold H, et al. 3,3'-Diiodothyronine concentrations in the sera of patients with nonthyroidal illnesses and brain tumors and of healthy subjects during acute stress. J Clin Endocrinol Metab 1998; 83(9): 3071-7.

EQUIVALENTS

The invention has been described broadly and generically herein. Those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention. Further, each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

INCORPORATION BY REFERENCE

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

What is claimed is:

1. A method of simultaneously assaying thyroxine ($T_4$), triiodothyronine ($T_3$), 3,3'-diiodo-L-thyronine (3,3'-$T_2$), and 3-iodothyronamine ($T_1AM$), comprising:
    a) providing a test sample, wherein the test sample comprises $T_4$, $T_3$, 3,3'-$T_2$, and $T_1AM$;
    b) providing a calibration sample, wherein the calibration sample comprises known quantities of reference $T_4$, $T_3$, 3,3'-$T_2$, and $T_1AM$;
    c) combining the test sample with the calibration sample;
    d) determining by mass spectrometry the quantity of $T_4$, $T_3$, 3,3'-$T_2$, and $T_1AM$ in the test sample and the quantity of the reference $T_4$, $T_3$, 3,3'-$T_2$, and $T_1AM$; and
    e) calibrating the quantity of the $T_4$, $T_3$, 3,3'-$T_2$, and $T_1AM$ in the test sample against the known and determined quantities of the reference $T_4$, $T_3$, 3,3'-$T_2$, and $T_1AM$ in the calibration sample.

2. The method of claim 1, wherein each of the reference $T_4$, $T_3$, 3,3'-$T_2$, and $T_1AM$ is differentially labeled with one or more mass spectrometrically distinct groups, such that each of the test sample $T_4$, $T_3$, 3,3'-$T_2$, and $T_1AM$ and each of the reference $T_4$, $T_3$, 3,3'-$T_2$, and $T_1AM$ can be distinguished by mass spectrometry.

3. The method of claim 2, wherein each of the reference $T_4$, $T_3$, 3,3'-$T_2$, and $T_1AM$ is radioisotopically labeled.

4. The method of claim 3, wherein the reference $T_4$ is deuterium-labeled $T_4$.

5. The method of claim 3, wherein the reference $T_3$ is $^{13}C$-labeled $T_3$.

6. The method of claim 3, wherein the reference 3,3'-$T_2$ is $^{13}C$-labeled 3,3'-$T_2$.

7. The method of claim 3, wherein the reference $T_1AM$ is deuterium-labeled $T_1AM$.

8. The method of claim 1, further comprising separating components of the combined sample of step (c) by liquid chromatography prior to step (d).

9. The method of claim 1, wherein the test sample is selected from the group consisting of blood, serum, plasma, amniotic fluid, and cerebrospinal fluid.

10. The method of claim 1, wherein the test sample further comprises reverse $T_3$ ($rT_3$); the calibration sample further comprises a known quantity of reference $rT_3$; the determining further comprises determining by mass spectrometry the quantity of $rT_3$ in the test sample and the quantity of the reference $rT_3$; and the calibrating further comprises calibrating the quantity of the $rT_3$ in the test sample against the known and determined quantity of the reference $rT_3$ in the calibration sample.

11. The method of claim 1, wherein the detection limit for $T_1AM$ in the test sample is 2.5 pg/mL (7.0 pmol/L).

12. The method of claim 1, wherein the quantitation limit for $T_1AM$ in the test sample is 4.0 pg/mL (11.3 pmol/L).

13. The method of claim 1, wherein the detection limit for 3,3'-$T_2$ in the test sample is 2.5 pg/mL (4.8 pmol/L).

14. The method of claim 1, wherein the quantitation limit for 3,3'-$T_2$ in the test sample is 4.0 pg/mL (7.6 pmol/L).

15. The method of claim 1, wherein the detection limit for $T_3$ in the test sample is 1.5 pg/mL (2.3 pmol/L).

16. The method of claim 1, wherein the quantitation limit for $T_3$ in the test sample is 3.0 pg/mL (4.6 pmol/L).

17. The method of claim 1, wherein the detection limit for $T_4$ in the test sample is 1.0 pg/mL (1.3 pmol/L).

18. The method of claim 1, wherein the quantitation limit for $T_4$ in the test sample is 1.8 pg/mL (2.3 pmol/L).

* * * * *

UNITED STATES PATENT AND TRADEMARK OFFICE
CERTIFICATE OF CORRECTION

PATENT NO. : 9,012,835 B2
APPLICATION NO. : 13/881602
DATED : April 21, 2015
INVENTOR(S) : Steven J. Soldin et al.

It is certified that error appears in the above-identified patent and that said Letters Patent is hereby corrected as shown below:

In the Specification

Column 1, Line 7-10:
"This invention was made with government support under NIH GCRC grant M01-RR-020359 and NICHD grant 5U10HD047890-03NIH. The government has certain rights in this invention."

Should read:
--This invention was made with government support under grant numbers NS047890, RR020359 awarded by the National Institutes of Health. The government has certain rights in the invention.--

Signed and Sealed this
Thirty-first Day of October, 2023

Katherine Kelly Vidal
*Director of the United States Patent and Trademark Office*